US008478607B2

(12) United States Patent
Bachik et al.

(10) Patent No.: US 8,478,607 B2
(45) Date of Patent: Jul. 2, 2013

(54) HOSPITAL SERVICE LINE MANAGEMENT TOOL

(75) Inventors: Scott E. Bachik, Cranberry Township, PA (US); Michelle R. Bianco, Pittsburgh, PA (US)

(73) Assignee: Accelero Health Partners, LLC, Canonsburg, PA (US)

( * ) Notice: Subject to any disclaimer, the term of this patent is extended or adjusted under 35 U.S.C. 154(b) by 335 days.

(21) Appl. No.: 12/646,539

(22) Filed: Dec. 23, 2009

(65) Prior Publication Data

US 2010/0169113 A1 Jul. 1, 2010

Related U.S. Application Data

(60) Provisional application No. 61/140,472, filed on Dec. 23, 2008.

(51) Int. Cl.
*G06Q 50/00* (2012.01)

(52) U.S. Cl.
USPC .......................................... 705/2

(58) Field of Classification Search
USPC .............................. 705/1, 2, 3, 10
See application file for complete search history.

(56) References Cited

U.S. PATENT DOCUMENTS

2004/0193476 A1* 9/2004 Aerdts ............................. 705/10
2007/0021967 A1* 1/2007 Jaligama et al. ................. 705/1

OTHER PUBLICATIONS

Pennsylvania Health Care Quality Alliance Quality Measures.*
Pennsylvania Health Care Quality Alliance Progress & Performance Report.*
Pennsylvania Health Care Quality Alliance Quality Measures—Hearth Attack (Sep. 13, 2008).*
Pennsylvania Health Care Quality Alliance Progress & Performance Report for Abington Memorial Hosptial (Jun. 18, 2008).*
Pennsylvania Health Care Quality Alliance Quality Measures—Infection Prevention (Sep. 11, 2008).*
Pennsylvania Health Care Quality Alliance Quality Measures—Pneumonia (Sep. 11, 2008).*
Pennsylvania Health Care Quality Alliance Quality Measures—Heart Failure (Jun. 19, 2008).*
Article: "Hospital report cards: Making the grade", first printed in the Jun. 2004 issue of the Harvard Health Letter, http://www.health.harvard.edu/newsweek/Hospital_report_cards_making_the_grade.htm.
Brochure—Human Motion Institute, The Experts in Musculoskeletal Service Line Management, www.humanmotioninstitute.com.
Conference Registration Form and Information "Capture the Power of Orthopaedics", Sponsored by: The Human Motion Institute, Feb. 26-27, 2001, Orlando, Florida.
Conference Registration Form and Information "Capture the Power of Orthopaedics", Sponsored by: The Human Motion Institute and Solucient, Oct. 15-16, 2001, Las Vegas, Nevada.
Conference Registration Form and Information "Capture the Power of Orthopaedics", Sponsored by: The Human Motion Institute and Solucient, Feb. 3-4, 2003, Las Vegas, Nevada.
Conference Registration Form and Information "Capture the Power of Orthopaedics", Sponsored by: The Human Motion Institute and Solucient, Feb. 16-17, 2004, Las Vegas, Nevada.

(Continued)

*Primary Examiner* — John Pauls
(74) *Attorney, Agent, or Firm* — Schwegman, Lundberg & Woessner P.A.

(57) ABSTRACT

A method for managing, organizing, integrating, and evaluating a service line of a hospital. Primary goals of the present method include, for example, improving patient care, increasing financial margins, and building volume.

25 Claims, 4 Drawing Sheets

OTHER PUBLICATIONS

Conference Registration Form and Information "Capture the Power of Orthopaedics", Sponsored by: The Human Motion Institute and Solucient, Mar. 3-4, 2005, Orlando, Florida.

Conference Form and Information "Capture the Power of Orthopaedics", Sponsored by: The Human Motion Institute, Mar. 13-14, 2007, Phoenix, Arizona.

Conference Form and Information "Capture the Power of Orthopaedics", Sponsored by: The Human Motion Institute, Feb. 11-12, 2008, Orlando, Florida.

Human Motion Institute Presentation "Capture the Power" Human Motion Institute, Sep. 2006.

Human Motion Institute Presentation "Musculoskeletal Service Line FY 07 Annual Report", Jul. 1, 2006-Jun. 30, 2007, presented Oct. 5, 2007.

Human Motion Institute Presentation "Neuromusculoskeletal Service Line ", Presented Oct. 8, 2008.

* cited by examiner

| Categories 10 | Subcategories 12 | Subsets 14 | Raw Scores 15 | Percentage Scores | | Overall Score 20 |
| --- | --- | --- | --- | --- | --- | --- |
| | | | | Subcategory Scores 16 | Category Scores 18 | |
| Reinforce Service Line Infrastructure 10a | | | | | 62% | 37% |
| Strengthen Customer Service 10b | | | | | 44% | |
| Balance Goals 10c | | | | | 44% | |
| Engage Physicians 10d | Value to Physicians 12a | | | | 38% | |
| | Physician Leadership 12b | Key physicians actively engaged in service line's leadership structure 14a | 2 / 2 | 50% (3 / 6) | | |
| | | Service line-specific physician leadership structure collaborates with hospital on service line initiatives (e.g., strategic planning, care, margins, and volumes) 14b | 1 / 2 | | | |
| | | Key physicians effectively influence peers in supporting service line goals 14c | 0 / 2 | | | |
| | Physician Engagement Plan 12c | | | | | |
| | Percentage of Targeted Physicians Actively Engaged 12d | | | | | |
| Integrate Referral Sources 10e | | | | | 17% | |
| Link Care Continuum 10f | | | | | 33% | |
| Build Brand Strategy 10g | | | | | 23% | |

FIGURE 2

HOSPITAL SERVICE LINE MANAGEMENT TOOL

CROSS-REFERENCE TO RELATED APPLICATION

This application claims priority from U.S. Provisional Patent Application No. 61/140,172, entitled "Hospital Service Line Management Tool," filed on Dec. 23, 2008, by the same inventors hereof, the disclosure of which is expressly incorporated herein by reference.

BACKGROUND

1. Field of the Invention

The present invention relates to a method for managing and evaluating a hospital. More particularly, the present invention relates to a method for managing and evaluating a specific service line of a hospital.

2. Description of the Related Art

Government agencies, health insurance companies, and consumers, have a desire to be informed of hospital performance data. Corporations and other organizations, such as U.S. News & World Report, compare and rank hospitals to one another based on certain evaluation criteria and report this information to the public.

The hospital itself also has a desire to be informed of its own performance data to improve patient care, increase financial margins, and build volume.

SUMMARY

The present invention provides a method for managing, organizing, integrating, and evaluating a service line of a hospital. The primary goal of this method is to create a program of distinction for the service line by programmatically improving patient care, increasing financial margins, and building volume, for example. The method involves identifying gaps or opportunities for improvement and strategically resolving those gaps to create a program of distinction.

According to an embodiment of the present invention, a method is provided for managing and evaluating a service line of a hospital. The method includes the steps of: collecting data relevant to the service line of the hospital; awarding the service line of the hospital a raw score out of a possible score in each of a plurality of categories based on the collected data; calculating a percentage score by dividing the sum of the raw scores for the plurality of categories by the sum of the possible scores for the plurality of categories; associating the percentage score with a stage of maturation; and reporting the stage of maturation to the hospital.

According to another embodiment of the present invention, a method is provided for managing and evaluating a service line of a hospital. The method includes the steps of: collecting data relevant to the service line of the hospital; awarding the service line of the hospital a raw score out of a possible score in each of a plurality of categories based on the collected data; classifying the service line of the hospital in one of an infancy stage, a development stage, and a maturity stage based on the sum of the raw scores for the plurality of categories; and providing feedback to the hospital based on the classifying step.

According to yet another embodiment of the present invention, a method is provided for managing and evaluating a service line of a hospital. The method includes the steps of: collecting data relevant to the service line of the hospital; evaluating the service line of the hospital in a plurality of categories, the plurality of categories selected from the group consisting of: patient care, infrastructure, customer service, strategic goal planning, physician engagement, referral sources, and brand strategy; classifying the service line of the hospital in one of an infancy stage, a development stage, and a maturity stage for each of the plurality of categories; and providing feedback to the hospital based on the classifying step.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2 is a chart illustrating a scoring step of the present method;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

A hospital is an institution for providing health care treatment to patients. The hospital may be divided into departments, also referred to as service lines, depending on the type of health care being provided. These service lines may include orthopedics, cardiovascular, oncology, neuroscience, and women's health, for example. Each service line may be further divided into product lines or specialties. For example, a musculoskeletal service line may include the following product lines: joint replacement, spine care, hand and upper extremity, foot and ankle, rehabilitation, and sports medicine, depending on the type of procedures being performed.

Figure 1:
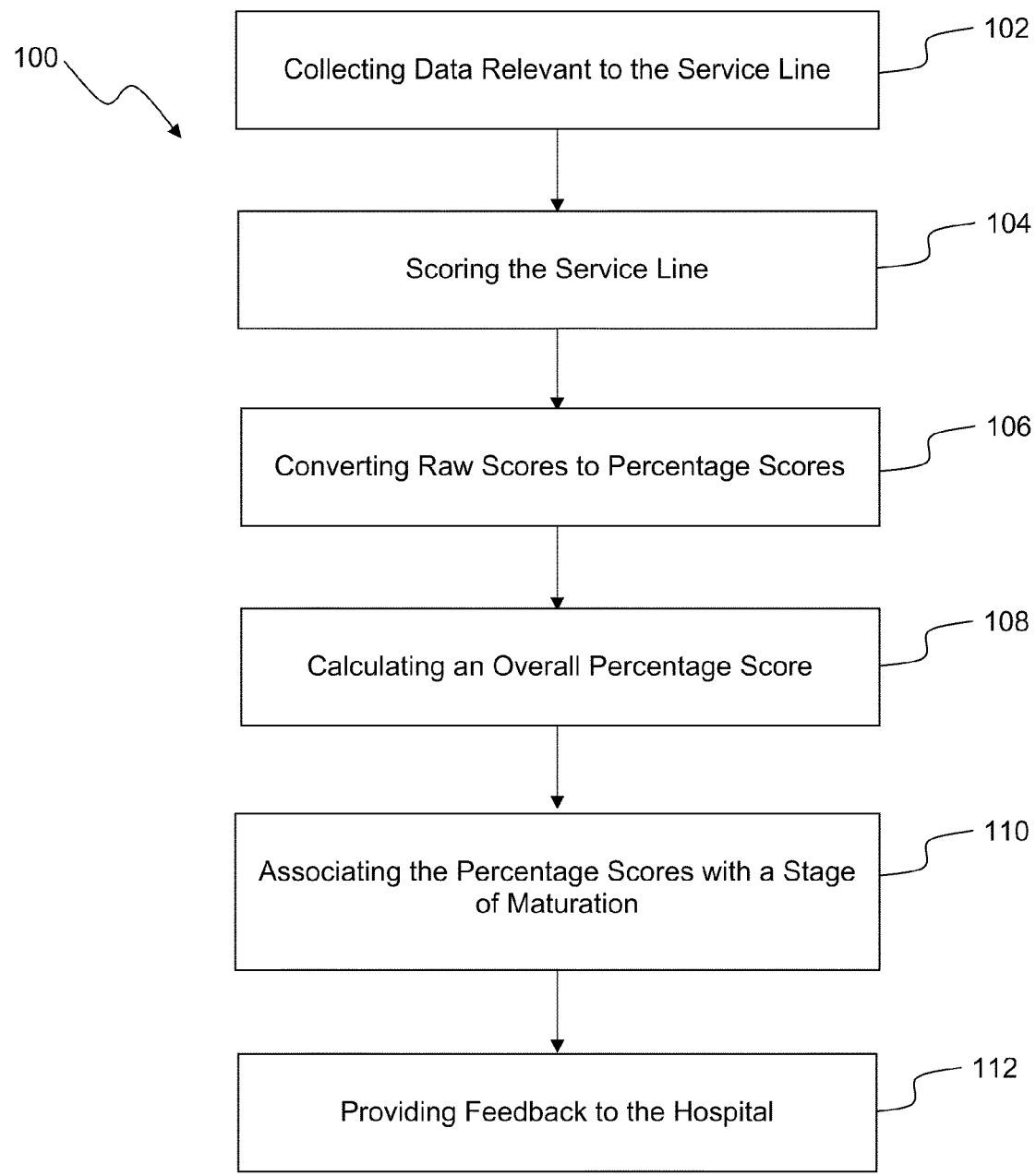
FIG. 1 is a flow diagram of an exemplary method of the present invention.

Referring to FIG. 1, the present invention provides an exemplary method 100 for managing, organizing, integrating, and evaluating a service line of a hospital. Primary goals of the present method include, for example, improving patient care, increasing financial margins, and building volume, to create a program of distinction.

Beginning with block 102 of FIG. 1, a first step of the present method involves collecting data and programmatic information relevant to a service line of a hospital. The step of collecting data and programmatic information relevant to the service line may involve, for example, making personal observations, gathering demographic data from the surrounding geographic area, inspecting hospital facilities, interviewing hospital staff, administrators, and referral sources, analyzing financial data (such as market share), analyzing patient care data, and evaluating competitors of the hospital. According to an exemplary embodiment of the present invention, the data collected should reflect strengths, weaknesses, opportunities, and potential threats to the service line of the hospital.

Continuing to block 104 of FIG. 1, another step of the present method involves scoring the service line of the hospital. Specifically, the scoring step involves scoring the service line of the hospital in a plurality of categories 10, as shown in FIG. 2. For example, categories 10 may include a Reinforce Service Line Infrastructure category 10a, a Strengthen Customer Service category 10b, a Balance Goals category 10c, an Engage Physicians category 10d, an Integrate Referral Sources category 10e, a Link Care Continuum category 10f, and a Build Brand Strategy category 10g. According to an exemplary embodiment of the present invention, categories 10 represent overarching goals of the service line of the hospital.

To facilitate the scoring step of block 104 of FIG. 1, categories 10 may be divided into subcategories 12, as shown in FIG. 2. Subcategories 12 may be key elements of the care continuum. For example, the Engage Physicians category 10d may be divided into a Value to Physicians subcategory 12a, a Physician Leadership subcategory 12b, a Physician Engagement Plan subcategory 12c, and a Percentage of Targeted Physicians Actively Engaged subcategory 12d.

To further facilitate the scoring step of block 104 of FIG. 1, subcategories 12 may be divided into subsets 14, as shown in FIG. 2. For example, the Physician Leadership subcategory 12b may be divided into subsets 14a, 14b, and 14c. According to an exemplary embodiment, subset 14a is used to evaluate the extent to which key physicians are actively engaged in the service line's leadership structure and collaborate with the hospital in the development of the service line's strategic plan; subset 14b is used to evaluate the extent to which a service line-specific physician leadership structure collaborates with the hospital on service line initiatives, including strategic planning and care, margin, and volume initiatives; and subset 14c is used to evaluate the extent to which key physicians effectively influence peers in supporting efforts to positively impact the service line's goals.

The Reinforce Service Line Infrastructure category 10a of FIG. 2 may be divided into subcategories and subsets as set forth in Table 1 below.

TABLE 1

Reinforce Service Line Infrastructure Category

| Subcategories | Subsets |
| --- | --- |
| Administrative Commitment | Dedicated resources/capital to service line; communications regarding service line by senior leadership throughout the organization. |
| | Administrative senior leader for service line. |
| | Administration meets quarterly with key service line individuals (e.g., reviews key service line indicators/initiatives, determines key strategic focus of service line, and provides mandates). |
| | Annual strategy sessions. |
| | Senior leadership oversight of strategic plan. |
| Physician Leadership | Key physician(s) in leadership roles (formal or informal); key physician(s) effectively drive change among peers. |
| | Routine vehicle for physician leader(s) to collaborate with peers and hospital leadership to address on-going developments. |
| | Physician leader(s) have integral role in establishing strategic plan, budget, and volume growth projections for service line. |
| Operational Support | Service line management structure/teams (e.g., reporting structure, vehicle to delegate/assess service line execution tactics). |
| | Service line director dedicated full-time to program; defined role and responsibilities. |
| | Service line infrastructure operation (e.g., tracks key metrics, develops action plans, drives improved performance measures). |
| | Service line management structure manages performance of service line and budget. |

The Strengthen Customer Service category 10b of FIG. 2 may be divided into subcategories and subsets as set forth in Table 2 below.

TABLE 2

Strengthen Customer Service Category

| Subcategories | Subsets |
| --- | --- |
| Customer Service Commitment | Established customer service principles from senior leadership. |
| | Customer service "champion" position for service line. |
| | Senior leadership ensures effective execution of service line customer service program. |
| | Customer service goals incorporated into service line managers' and key department leaders' annual performance plans. |
| Customer Service Infrastructure and Process | Key departments within service line educated on customer service (e.g., vision, principles, process, and goals). |
| | Customer service principles shared within organization. |
| | Detailed customer service actions established by job function. |
| | Customer service guide effectively communicated (at least annually). |
| | Customer satisfaction teams at service line or department level. |
| | New employees educated on customer service (e.g., approaches and tools). |

TABLE 2-continued

Strengthen Customer Service Category

| Subcategories | Subsets |
|---|---|
| Customer Service Metrics | Standardized measuring tools utilized at a department/unit level (e.g., Press Ganey, Hospital Consumer Assessment of Healthcare Providers and Systems (H-CAHPS), Surgical Care Improvement Project (SCIP), Joint Commission on the Accreditation of Healthcare Organizations (JCAHO), Premier, Leapfrog) Standardized scores for department-level programs have acceptable return rate (e.g., >85%). Standardized scores tracked and shared at department level. Standardized scores managed and improved through customer service team. Service line scores consistently at or above goal. Standardized scores leveraged to internal and external stakeholders. |
| Average | 2-quarter average for standardized, third-party scores (e.g., below $50^{th}$ percentile = 0; $50^{th}$-$74^{th}$ percentile = 1; $75^{th}$ percentile and above = 2). |

The Balance Goals category 10c of FIG. 2 may be divided into subcategories and subsets as set forth in Table 3 below.

TABLE 3

Balance Goals Category

| Subcategories | Subsets |
|---|---|
| Care | Participation in national and regulatory programs; results utilized to drive change within organization. |
| | Physicians and direct care providers involved in patient outcome metrics. |
| | Patient outcomes (including customer service), metrics, and goals established, tracked, and communicated at unit or condition level (e.g., joint replacement, spinal care). |
| | Process improvement plan for patient outcomes metrics; results used to create operational or clinical change. |
| | Track patient outcomes by diagnosis; results used to create operational and clinical change. |
| | Patient outcomes leveraged internally and externally. |
| Margin | Service line margin goals established, managed, and communicated by product line. |
| | Service line manager manages cost and revenue opportunities and routinely reports variances to senior leadership. |
| | Infrastructure executes change to enhance margins. |
| Volume | Volume growth goals attached to market share goals in primary, secondary and total service area. |
| | Volume growth goals established through collaboration of physicians and key service line departments (e.g., operating room and unit nurse director). |
| | Volume growth goals defined, tracked and routinely reported through key leadership group (minimum of quarterly). |
| | Tactical execution plan to achieve growth plan. |
| | Implications of additional resources, facilities, and care understood; action plan developed to support volume growth. |

The Engage Physicians category 10d of FIG. 2 may be divided into subcategories and subsets as set forth in Table 4 below.

TABLE 4

Engage Physicians Category

| Subcategories | Subsets |
|---|---|
| Relationship/ Program Value to Physicians | Physicians perceive value in being actively involved in decisions affecting patient care. |
| | Physicians perceive value in being associated with programming and collateral/educational materials of service line. |
| | Key physicians link own success (e.g., quality of care, volume, and finances) to service line success. |
| Physician Leadership | Key physicians actively engaged in service line specific leadership structure and collaborate in development of service line strategic plan. |
| | Service line-specific physician leadership structure collaborates with hospital on service line initiatives (e.g., strategic planning, care, margins, and volumes). |
| | Key physicians effectively influence peers in supporting service line goals. |

TABLE 4-continued

Engage Physicians Category

| Subcategories | Subsets |
| --- | --- |
| Physician Engagement Plan | Service line-specific physician engagement plan including both short and long term strategies.<br>Physician engagement plan pro-actively implemented.<br>Physician engagement plan routinely (at least annually) evaluated and modified. |
| Targeted Physicians Engaged | Targeted physicians actively engaged (e.g., 0-20% = 0; 21-50% = 1; 51-100% = 2). |

The Integrate Referral Sources category 10e of FIG. 2 may be divided into subcategories and subsets as set forth in Table 5 below.

TABLE 5

Integrate Referral Sources Category

| Subcategories | Subsets |
| --- | --- |
| Resource | Data collection process for referring physicians (e.g., collection during admission process) used to develop integrated referral source plan.<br>Service line referral base understood by physician specialty (e.g., joint replacement, spinal care, etc.).<br>Referral base extends beyond primary care physicians (PCP's) (i.e., includes rheumatology, physiatry, emergency departments (ED), occupational medicine, certified athletic trainers (ATC's), community resources, etc.).<br>Defined goals for referrals by product line.<br>Physician liaison communicates services and capabilities to existing and potential referral sources. |
| Integration | Needs, wants, and expectations of top referral sources understood.<br>Clear vision and plan for integrating referral sources.<br>Physicians share referral information with hospital.<br>Volume increase in base and new referrals.<br>Education by specialty occurs routinely (at least twice per year).<br>Objective data (e.g., patient satisfaction, patient outcomes) leveraged with referral sources. |

With respect to the Link Care Continuum category 10f of FIG. 2, each product line of a service line may be evaluated independently. For example, for a musculoskeletal service line, the joint replacement product line, spine care product line, rehabilitation product line, and sports medicine product line may be evaluated independently.

To evaluate a joint replacement product line, the Link Care Continuum category 10f of FIG. 2 may be divided into subcategories and subsets as set forth in Table 6 below.

TABLE 6

Link Care Continuum Category for Joint Replacement Product Line

| Subcategories | Subsets |
| --- | --- |
| Community Integration | Action plan to transport target audience and service area patients into care continuum.<br>Promotes community programming/education (e.g., 4 times per year) to highlight joint pain prevention and management and joint replacement.<br>Coordinated care processes to integrate community-based referral sources (e.g., assisted living facilities (ALF's), skilled nursing facilities (SNF's)).<br>Internal education for volunteers and hospital employees to showcase joint replacement program, surgeons, and ancillary care providers. |
| Integration of Physician Referral Sources | Hospital tracks referral source on admission.<br>Deliberate processes to integrate and increase surgeon referrals.<br>Joint pain care algorithm to facilitate medical management and surgical referrals.<br>Referral source relationships with sub-specialties to improve quality of referrals.<br>Continuing medical education (CME) program for referring physicians, extenders, and sub-specialties. |
| Surgeon | Physician leadership support for clinical decision making. |

TABLE 6-continued

Link Care Continuum Category for Joint Replacement Product Line

| Subcategories | Subsets |
|---|---|
| Relationships | Pre-operative education provided by physician (e.g., surgical procedure education, patient experience education). |
| | Needs, wants, and expectations related to programmatic and clinical goals defined and prioritized. |
| | Surgeon's office linked to hospital for streamlined scheduling. |
| | Admitting history and physical (H&P) process involves PCP, surgeon, and hospital requirements; updated within 24 hours of admission. |
| | Operating room efficiencies identified. |
| | Operating room standards of care and processes established. |
| | Surgeon's joint replacement cases aggregated to defined days of the week. |
| | Patient outcomes metrics established when surgical referral is identified. |
| | Collateral materials to support physician volume growth. |
| | Physician marketed to brand/program (e.g., provider of joint replacement). |
| Hospital Services (Pre-Surgical Services) | Pre-admission testing protocol process standardized for specific patient population (e.g., inclusive of anesthesia education and assessment). |
| | Standardized process to review results prior to surgical date. |
| | Standardized pre-admission education at hospital site. |
| Hospital Services (Day of Surgery) | Standardized pre-operative orders. |
| | Variation of physician preferences reduced. |
| | Comprehensive multi-disciplinary pain management protocols. |
| Hospital Services (Acute Care) | Joint program coordinator responsible for day-to-day operations of joint program and communication with senior leadership and physicians. |
| | Multi-disciplinary product line team to implement programmatic change. |
| | Key success metrics established, tracked, and communicated (e.g., dashboard and patient outcomes report card). |
| | Reporting of metrics and action plan is routine agenda item on nursing unit. |
| | Joint replacement nurse education training based on physician protocols. |
| | Standardized post-operative orders and clinical pathways; variances understood through routine chart audits. |
| | Discharge criteria communicated to patient upon admission. |
| | Patients aggregated on one patient unit with bed control support. |
| | Joint replacement surgeries migrated to Monday/Tuesday dates; care, resources and length of stay (LOS) consistent regardless of surgical day. |
| | Patient outcomes tracked and communicated to care team. |
| | LOS tracked and communicated to care team. |
| | Customer service program integrated at unit level. |
| Hospital Services (Post-Acute Care) | Established patient care goals. |
| | Integrated post-acute care services to ensure timely access to patient care. |
| Rehabilitation | Established patient protocols for Physical and Occupational Therapy. |
| | Patient progress within rehabilitation communicated with discharge planner to ensure timely discharge. |
| Distinction | Multi-disciplinary, pre-operative patient education classes (occur for >80% of patients). |
| | Block scheduling for pre-admission testing (PAT) to link between PAT and pre-operative education. |
| | Joint replacement nursing unit staff performs PAT through coordinated scheduling efforts. |
| | Branded and high quality educational materials related to pre-operative care process and hospital admission preparation. |
| | Patient "coach" role to encourage family support and participation during education, admission, and post-discharge care. |
| | Pre-operative physical therapy evaluation/strengthening program. |
| | Pre-operative case management integration. |
| | Segregated unit dedicated to joint replacement patients. |
| | Private rooms. |
| | Direct admission to unit allowing for pre-operative and post-operative care consistency. |
| | Dedicated nursing and rehabilitation staff. |
| | Joint replacement cases performed on Monday/Tuesday to ensure "group" approach to care. |
| | Unit based group therapy sessions. |
| | Celebratory event with patients and staff prior to discharge. |
| | Wellness approach promoting independence. |
| | Patient amenities to emphasize differentiation (e.g., welcome "gift," access to hairdresser prior to discharge). |
| | Annual patient recognition event (e.g., dinner/dance, golf outing). |
| | Specialty program certification (e.g., Joint Commission Disease specific care certification, Blue Cross program of distinction). |
| | Discharge goals identified and tracked (e.g., >80% of goal patients discharged). |

To evaluate a spine care product line, the Link Care Continuum category 10f of FIG. 2 may be divided into subcategories and subsets as set forth in Table 7 below.

TABLE 7

Link Care Continuum Category for Spine Care Product Line

| Subcategories | Subsets |
| --- | --- |
| Community Integration | Action plan to transport target audience and service area patients into care continuum. Promotes community programming/education (e.g., 3 times per year) to highlight low back pain prevention and management and surgical intervention options. Internal education for volunteers and hospital employees to showcase low back pain surgical and non-surgical care options, surgeons, and ancillary care providers. Referral call line tracks referrals and demographics; information leveraged to identify consumer needs. |
| Integration of Physician Referral Sources | Hospital tracks referral source on admission. Deliberate processes to integrate and increase surgeon referrals. Low back pain algorithm to facilitate medical management and surgical referrals. Referral source relationships with sub-specialties to improve quality of referrals. Referral source relationships with osteoporosis care providers (e.g., ob/gyn, endocrinology, interventional radiology, gerontology) to manage at-risk patient population. Emergency Department and hospitalists educated to spine care program and available clinical resources. CME program for referring physicians, extenders, and sub-specialties to improve patient care and access. |
| Surgeon Relationships | Physician leadership support for clinical decision making. Pre-operative education provided by physician (e.g., surgical procedure education, patient experience education). Needs, wants, and expectations related to programmatic and clinical goals defined and prioritized. Surgeon's office linked to hospital for streamlined scheduling. Admitting history and physical (H&P) process involves PCP, surgeon, and hospital requirements; updated within 24 hours of admission. Operating room efficiencies identified. Operating room standards of care and processes established (e.g., process to assess, approve, and implement new technology). Patient outcomes metrics established when surgical referral is identified. Collaborative marketing to attach physician to brand/program. Consistent inpatient vs. outpatient procedures based on care needs and payor trends. Financial and care implications communicated prior to transition from inpatient to outpatient procedures. Approaches coordinated between orthospine and neurospine. |
| Hospital Services (Emergency Services) | Consistent admission criteria for back pain patients. Clinical criteria for assessment and admission of vertebral fracture patients; coordinated scheduling of outpatient procedures. Referral process for non-admitted back pain patients. Process for off-hours Emergency Department visits. |
| Hospital Services (Pre-Surgical Services) | Pre-admission testing protocol process standardized for specific patient population (e.g., inclusive of anesthesia education and assessment). Standardized process to review results prior to surgical date. Standardized surgical spine pre-admission education at hospital site. Bracing needs identified and/or obtained prior to admission. |
| Hospital Services (Day of Surgery) | Standardized pre-operative orders. Variation of physician preferences reduced. Post-op care transfer from post anesthesia care unit (PACU) to nursing unit. |
| Hospital Services (Outpatient Surgery) | Consistent written discharge instructions demonstrating progressive mobility. Surgical start time conducive to recovery in outpatient area. Post-operative referrals provided upon discharge. |
| Hospital Services (Acute Care) | Spine program coordinator responsible for day-to-day operations of spine program and communication with senior leadership and physicians. Multi-disciplinary product line team to implement programmatic change. Key success metrics established, tracked, and communicated (e.g., LOS tracking, dashboard and patient outcomes report card). Reporting of metrics and action plan is routine agenda item on nursing unit. Surgical spine nurse education training based on physician protocols. Standardized post-operative orders and clinical pathways; variances understood. Discharge criteria communicated to patient upon admission. Patients aggregated on one patient unit with bed control support regardless of surgical specialty (e.g., neurospine vs. orthospine). Patient outcomes tracked and communicated to care team. LOS tracked and communicated to care team. Customer service program integrated at unit level. Bracing provisions do not interfere with timely functional progression and patient discharge. |

TABLE 7-continued

Link Care Continuum Category for Spine Care Product Line

| Subcategories | Subsets |
| --- | --- |
| Inpatient Rehabilitation | Patient protocols established for physical and occupational therapy to support discharge goals.<br>Patient progress within rehabilitation communicated with discharge planner to ensure timely discharge.<br>Weekend rehabilitation services. |
| Outpatient Rehabilitation | Early intervention program for low back pain communicated to referral sources.<br>Patient outcomes tracked for surgical and non-surgical patient population; results leveraged with referral sources.<br>Occupational Medicine program linked to outpatient rehabilitation services.<br>Pain management linked to outpatient rehabilitation services. |
| Coordination | Care coordination model for consistent approach from point of referral through treatment.<br>Care algorithm for assessment and recommendations.<br>Care algorithm developed in collaboration with surgeon, primary care, pain management, physiatry, and rehabilitation.<br>Referral guidelines consistently utilized for PCP's and specialty services.<br>Methods for effective communication of patient care between providers.<br>Patient outcome measures on non-surgical patients collected, managed, and leveraged.<br>Triage call line for individuals with spine care needs.<br>Triage calls tracked and used to improve referral relationships and to improve community education.<br>Care coordination model exists within physical space housing all services necessary to spine care continuum, if necessary.<br>Branded and high quality educational materials related to surgical and non-surgical care processes (e.g., exercise programs).<br>Segregated inpatient unit with private beds dedicated to spine services.<br>Hospital website houses spine care preventative materials.<br>Spine coordinator position to link care continuum, strengthen referral source relationships, track outcomes, and educate patients.<br>Specialty program certification (e.g., Joint Commission Disease specific care certification, Blue Cross program of distinction). |

To evaluate a rehabilitation product line, the Link Care Continuum category 10f of FIG. 2 may be divided into subcategories and subsets as set forth in Table 8 below.

TABLE 8

Link Care Continuum Category for Rehabilitation Product Line

| Subcategories | Subsets |
| --- | --- |
| Care | Specially trained outpatient rehabilitation clinicians (e.g., advanced degrees, continuing education, and experience).<br>Internal education (e.g., at least one time per month).<br>High-volume referral sources engaged (e.g., at least two times per year) to speak to rehabilitation staff on advanced surgical techniques, rehabilitation intervention guidelines, and expected rehabilitation outcomes.<br>Budget allocated to continuing education for rehabilitation.<br>Branded home exercise programs and instructions.<br>Patient outcomes (including functional and patient perception of care) tracked by condition.<br>Patient outcomes used to establish clinical best practices and operational opportunities for improvement.<br>Patient outcomes used as performance indicator for annual reviews.<br>Documentation accurately represents care provided during patient visits, as evidenced by routine peer review process.<br>Timely access to initial evaluation care (e.g., 1 day = 2; 2 days = 1; >2 days = 0).<br>Timely patient care (e.g., average of 45-60 minutes = 2; 31-44 minutes = 1; <30 minutes = 0).<br>Sufficient staffing mix throughout hours of operation. |
| Margin | Performance-based metrics established, tracked, and communicated within rehabilitation department (e.g., monthly).<br>Rehabilitation staff understands goal of meeting or exceeding performance metrics (e.g., daily visits per therapist).<br>Margin metrics used to manage business (e.g., staff recruitment).<br>Performance metric goals defined with corresponding action plans.<br>Peer review to ensure documentation and charges accurately represent care provided and meet regulatory standards.<br>Effective processes to collect co-pays (e.g., collection rate verified at least monthly).<br>Contractual agreements for highest payors (e.g., procedure rate, percent of charges, visit rate, etc.). |

TABLE 8-continued

Link Care Continuum Category for Rehabilitation Product Line

| Subcategories | Subsets |
|---|---|
| Volume | Adequate procedures per visit (e.g., <2.2 procedures per visit = 0; >2.8 procedures per visit = 2).<br>Non-clinical time (e.g., documentation time) does not impede patient scheduling, access, or care.<br>Patient visit volumes tracked (e.g., on a monthly basis) by site, by discipline and by therapist, compared to goals, and shared with staff<br>Cancellations and no-shows tracked and reported (e.g., monthly).<br>Low cancellation and no-show rate (e.g., <12% = 2; 12-14% = 1; >15% = 0).<br>Referral sources captured by physician, diagnosis, and zip code.<br>Referral source data used to create business development strategies.<br>Marketing materials (e.g., brochures, clinical and customer service results) leveraged to grow business.<br>Resources (e.g., director, manager, staff) with defined business growth strategy plans.<br>Average visits per referral reviewed. |

To evaluate a sports medicine product line, the Link Care Continuum category 10f of FIG. 2 may be divided into subcategories and subsets as set forth in Table 9 below.

TABLE 9

Link Care Continuum Category for Sports Medicine Product Line

| Subcategories | Subsets |
|---|---|
| Community Integration | Action plan to transport target audience and service area patients (e.g., active lifestyle, coaches, recreational leagues, school districts, and pro/semi-pro sports) into care continuum.<br>Relationships with school districts and ATC's defined; referral patterns understood and leveraged.<br>Programming to highlight sports medicine topics (e.g., run/walk, golf outings) about 4-6 times per year.<br>Internal education for volunteers and hospital employees for sports medicine topics and services.<br>Sports medicine services highlighted at community events (e.g., 5K runs, golf outings).<br>Educational materials developed to accompany programming; product line brochure to highlight services and capabilities.<br>Process for identifying patients with school district ties for notifying ATC and/or surgeon.<br>Referral call line tracks referrals and demographics; information leveraged. |
| Integration of Physician Referral Sources | Hospital tracks referral sources for outpatient surgical patients through database.<br>Referral source information utilized to enhance existing relationships and to develop others.<br>Sports medicine physicians and rehabilitation professionals educate referral sources (e.g., PCP's) to knee and shoulder pain care algorithms.<br>Relationship and processes exists between ED and sports medicine physicians.<br>Referral source relationships with school districts, coaches, and ATC's.<br>Tracking by patient/referral source for contractual relationships.<br>CME program for PCP's and extenders (e.g., at least 1 time per year). |
| Surgeon Relationships | Key surgeons positioned as leaders in program development.<br>Needs, wants, and expectations related to programmatic and clinical goals defined and prioritized.<br>Surgeon's office effectively linked to hospital for streamlined scheduling.<br>Operating room efficiencies identified.<br>Operating room standards of care and processes established.<br>Consistent inpatient vs. outpatient procedures based on care needs and payor trends.<br>Established relationship with durable medical equipment (DME) provider to ensure timely receipt of bracing; process coordinated through physician's office prior to admission.<br>Collaborative marketing to attach physician to brand/program. |
| Hospital Services | Multi-disciplinary product line team to implement programmatic change.<br>Key success metrics established, tracked, and communicated (e.g., case volume, referrals, variable cost). |
| Hospital Services (Emergency Services) | Fast-track program for injured athletes (especially those referred by ATC).<br>Referral process for non-surgical patients based on condition. |
| Hospital Services (Pre-Surgical Services) | Bracing needs and post-operative physical therapy consultation identified prior to admission. |

TABLE 9-continued

Link Care Continuum Category for Sports Medicine Product Line

| Subcategories | Subsets |
| --- | --- |
| Hospital Services (Day of Surgery) | Standardized pre-operative orders.<br>Reduced variation of physician preferences.<br>Process for same-day transfer from post-operative care to recovery area.<br>Written, branded, and diagnosis-specific discharge instructions (e.g., bracing instructions, pain management instructions) demonstrate progressive mobility.<br>Surgical times coordinated to allow for post-operative recovery in outpatient area.<br>Post-operative referrals provided upon discharge |
| Hospital Services (Imaging) | Timely access to imaging services. |
| Rehabilitation | Timely access to outpatient rehabilitation for sports medicine patients (e.g., typically 24 hours); direct physical therapist referrals with same-day access.<br>Post-operative patient protocols for outpatient physical therapy.<br>Effective communication process between outpatient physical therapy and sports medicine physicians to support return to work/activity.<br>Early intervention program for non-surgical care communicated to referral sources via care algorithms.<br>Patient outcomes tracked for surgical and non-surgical patient populations; results leveraged with referral sources.<br>Outpatient rehabilitation environment, equipment, and resources support comprehensive sports medicine population needs.<br>Strategic plan for outpatient rehabilitation system expansion. |

The Build Brand Strategy category 10g of FIG. 2 may be divided into subcategories and subsets as set forth in Table 10 below.

TABLE 10

Build Brand Strategy Category

| Subcategories | Subsets |
| --- | --- |
| Overall | Marketing budget including service line specific program development activities.<br>Marketing plan with dates and responsibilities.<br>Standing meetings to review current initiatives, marketing plan, and new materials.<br>Senior administration team engaged in development of brand strategy. |
| Brand Establishment and Development | Brand/logo adopted and used to reinforce brand identity and continuity throughout continuum.<br>Sub-brands for program product lines supported with a name and logo.<br>Musculoskeletal website implemented with program specific information (e.g., specialties, physicians, locations).<br>Consumer advertising/promotion via various forms of media to create awareness in the community.<br>Action plan to make consumer/patient's first experience a positive one; consumer inquiries tracked to evaluate success of activities/promotions. |
| Internal Awareness | Internal communications distributed to all levels of organization.<br>Volunteers integrated to serve as active voice in the community.<br>Internal event/open house for staff members to interface with service line team and clinical staff. |
| Brand Relationship between Hospital and Physicians | Physician guide distributed to introduce capabilities of program and physicians.<br>Liaison educated to distribute materials and to receive feedback from physicians.<br>Physicians participate in programming to demonstrate breadth and depth of clinical staff capabilities.<br>Service line benefits marketed to physicians using outcomes, education, direct outreach, and CME. |
| Product Line Educational and Patient Materials | Service line brochures disseminated through hospital campus and other common areas in the community.<br>Educational packets for patients and families to serve as a guide to theit hospital experience.<br>Outcomes promoted (e.g., rehabilitation, customer service, clinical results) to differentiate hospital's services. |
| Targeted Community Marketing | Community calendar developed to link third-party organizations (e.g., Human Motion Institute (HMI)) into existing hospital wide events.<br>Regular lectures (e.g., 2-3 times yearly) by physicians and clinical staff to educate consumers on topics pertaining to musculoskeletal care.<br>Interactive/multi-station programming sessions (e.g., minimum of 2 per year) to highlight a variety of services within the musculoskeletal continuum. |

Referring still to FIG. 2, the scoring step of block 104 (FIG. 1) may involve scoring each category 10, subcategory 12, and/or subset 14, on a scale to produce raw score 15. An exemplary scale may include possible scores ranging from zero (0) to two (2). In an exemplary embodiment, a raw score 15 of zero (0) indicates that a category 10, subcategory 12, and/or subset 14, is not in existence; a raw score 15 of one (1) indicates that a category 10, subcategory 12, and/or subset 14, is not being executed effectively and/or consistently; and a raw score 15 of two (2) indicates that a category 10, subcategory 12, and/or subset 14, is being executed both effectively and consistently. As shown in FIG. 2, subset 14*a* was given a raw score 15 of two (2), subset 14*b* was given a raw score 15 of one (1), and subset 14*c* was given a raw score 15 of zero (0). According to an exemplary embodiment of the present invention, at least some of the data gathered during the collecting step of block 102 (FIG. 1) should provide information necessary to complete the scoring step of block 104 (FIG. 1).

Continuing to block 106 of FIG. 1, another step of the present method involves converting the raw scores 15 of block 104 to percentage scores. As shown in FIG. 2, to achieve a percentage score 16 for a subcategory 12, raw scores 15 within each subcategory 12 are added together and divided by a total possible score. Similarly, to achieve a percentage score 18 for a category 10, raw scores 15 within each category 10 are added together and divided by a total possible score. According to an exemplary embodiment of the present invention, the evaluator inputs the raw scores 15 into a computing device, and the computing device calculates the percentage scores.

In the example illustrated in FIG. 2, the raw scores 15 from the Physician Leadership subcategory 12*b*, specifically the raw score 15 of two (2) for subset 14*a*, the raw score 15 of one (1) for subset 14*b*, and the raw score 15 of zero (0) for subset 14*c*, are added together to achieve a total raw score of three (3). The total raw score of three (3) is then divided by the total possible score of six (6), resulting in a percentage score 16 for the Physician Leadership subcategory 12*b* of 50%. The same process was then repeated for each of the remaining subcategories 12 within the Engage Physicians category 10*d*, including the Value to Physicians subcategory 12*a*, the Physician Engagement Plan subcategory 12*c*, and the Percentage of Targeted Physicians Actively Engaged subcategory 12*d*.

Referring still to the example of FIG. 2, to achieve a percentage score 18 for the Engage Physicians category 10*d*, raw scores 15 from the Value to Physicians subcategory 12*a*, the Physician Leadership subcategory 12*b*, the Physician Engagement Plan subcategory 12*c*, and the Percentage of Targeted Physicians Actively Engaged subcategory 12*d*, are added together to achieve a total raw score. The total raw score is then divided by the total possible score, resulting in a percentage score 18 for the Engage Physicians category 10*d* of 38%. The same process is then repeated for each of the remaining categories 10, including the Reinforce Service Line Infrastructure category 10*a*, the Strengthen Customer Service category 10*b*, the Balance Goals category 10*c*, the Integrate Referral Sources category 10*e*, the Link Care Continuum category 10*f*, and the Build Brand Strategy category 10*g*.

Continuing to block 108 of FIG. 1, another step of the present method involves calculating an overall percentage score. To calculate an overall percentage score 20, the percentage scores 18 from the various categories 10 are averaged. According to this exemplary embodiment, the overall percentage score 20 is not weighted to favor a particular category 10 that may have a higher total raw score due to the number of subcategories 12 and/or subsets 14 within that category 10.

Referring still to the example of FIG. 2, to achieve an overall percentage score 20, percentage scores 18 from all of the categories 10 are averaged. Specifically, percentage scores 18 from the Reinforce Service Line Infrastructure category 10*a*, the Strengthen Customer Service category 10*b*, the Balance Goals category 10*c*, the Engage Physicians category 10*d*, the Integrate Referral Sources category 10*e*, the Link Care Continuum category 10*f*, and the Build Brand Strategy category 10*g*, are averaged to achieve an overall percentage score 20 of 37%. As mentioned above, the overall percentage score 20 is an average percentage score 18 of the various categories 10, such that the overall percentage score 20 is not weighted to favor a particular category 10. It is within the scope of the present invention, however, that certain categories 10 may be weighted to more strongly influence the overall percentage score 20. For example, the Reinforce Service Line Infrastructure category 10*a* and the Engage Physicians category 10*d* have been shown to have a strong correlation to a program's maturity, and therefore may be weighted in the overall percentage score 20.

Continuing to block 110 of FIG. 1, another step of the present method involves associating the percentage scores with a stage or level of maturation. The associating step of block 110 may be completed for percentage scores 16 of each subcategory 12, percentage scores 18 of each category 10, and/or overall percentage score 20. In an exemplary embodiment shown in FIG. 3, a percentage score between approximately 0% and 44% is associated with a first stage of maturation 30, a percentage score between approximately 45% and 79% is associated with a second stage of maturation 32, and a percentage score between approximately 80% and 100% is associated with a third stage of maturation 34. First stage of maturation 30 has been shown to indicate a program in a stage of infancy. Second stage of maturation 32 has been shown to indicate a program in a stage of development. Third stage of maturation 34 has been shown to indicate a program in a stage of maturity.

These maturation stages or levels were determined empirically by observing general characteristics of programs in stages of infancy, development, and maturity. For example, for the Physician Leadership subcategory 12*b*, the inventors determined that: (1) a program in the stage of infancy will generally have traditional medical staff in leadership positions with physicians working on product line specific initiatives that directly affect them; (2) a program in the stage of development will generally have key physicians in product line specific or service line specific leadership roles, and will generally have leadership roles that are clearly defined and productive, but will generally inconsistently engage other physicians in decision making; and (3) a program in the stage of maturity will generally have a comprehensive, well-defined and active service line leadership structure in place, the leadership structure will generally have accountability for care, margins, and volume metrics, and key physicians will generally influence others for service line success.

With respect to the Reinforce Service Line Infrastructure category 10*a* of FIG. 2, service lines in each stage of maturation have been observed to exhibit the general characteristics set forth in Table 11 below.

TABLE 11

Reinforce Service Line Infrastructure Category

| Subcategories | Maturation Stages | | |
| --- | --- | --- | --- |
| | Infancy | Development | Maturity |
| Administrative Commitment | Administrative focus on musculoskeletal service line is established. | Musculoskeletal service line is defined as high level priority (i.e. established as a signature service line). Senior leader in place with service line responsibility and authority to remove barriers to performance | Administration meets quarterly to review key service line indicators and initiatives and determines key strategic focus of service line. Annual strategy session occurs to ensure progression of service line. |
| Physician Leadership | Reasonable foundation for musculoskeletal physician leadership exists. | Intermittent (non-structured) interaction exists with Key Physicians and administration with regards to the service line. | Key Physicians are actively and consistently engaged in vision, budget and growth strategies for service line. Structured vehicle (i.e. quarterly meetings) exists for engagement. |
| Operational Support | Defined role/position exists to support service line (i.e. service line manager). Roles and responsibilities defined. | Service line management structure is deployed. Dedicated service line manager, key service line leadership team, integrated service line operations team, and product line teams in place to support the program. | Service line structure consistently implements, tracks and improved performance measures. Barriers are understood and action plans are consistently implemented. Management structure has the authority to manage the performance of the service line. |

With respect to the Strengthen Customer Service category 10*b* of FIG. 2, service lines in each stage of maturation have been observed to exhibit the general characteristics set forth in Table 12 below.

TABLE 12

Strengthen Customer Service Category

| Subcategories | Maturation Stages | | |
| --- | --- | --- | --- |
| | Infancy | Development | Maturity |
| Customer Service Commitment | Senior leadership has established a vision and customer service principles to support organizational goals. | Customer service champion has been established to assume responsibility, direction and success of customer service process. Execution of program is managed and monitored at a unit or department level. | Customer service is managed by service line and results are reviewed consistently by senior leadership. Service line customer service responsibility and authority exists. Customer service success is an objective goal incorporated into service line manager and key department leaders' annual performance plan. |
| Customer Service Infrastructure and Process | Vision and principles of customer service are shared within the organization and incorporated in the new hire orientation process. | Detailed actions to support customer service principles are established by job function for the service line. Customer service guide is in place and effectively communicated at a minimum annually. | Continual process improvement approach is established through customer satisfaction teams at a service line or department level to ensure longevity of program. Effective process exists to ensure new employees are effectively educated to customer service approach and tools. |

TABLE 12-continued

Strengthen Customer Service Category

| | Maturation Stages | | |
|---|---|---|---|
| Subcategories | Infancy | Development | Maturity |
| Customer Service Metrics | Standardized measuring tool is established and utilized at a department/unit level (i.e. Press Ganey, H-CAHPS). Trending of scores are tracked and shared at a department level. | Survey tool is specific to processes within control and implemented at a department level. Return rate is >85%. Service line goals are identified. Results are effectively managed and improved through the customer service team. | Service line results are consistently at or above goal. Results are effectively leveraged to internal and external stakeholders. Metrics are reviewed at a minimum, annually to re-evaluate for inclusion. |

With respect to the Balance Goals category 10c of FIG. 2, service lines in each stage of maturation have been observed to exhibit the general characteristics set forth in Table 13 below.

With respect to the Engage Physicians category 10d of FIG. 2, service lines in each stage of maturation have been observed to exhibit the general characteristics set forth in Table 14 below.

TABLE 13

Balance Goals Category

| | Maturation Stages | | |
|---|---|---|---|
| Subcategories | Infancy | Development | Maturity |
| Care | Patient Outcomes inclusive of patient satisfaction are tracked at a hospital level to support national and regulatory standards (i.e. H-CAHPS, JCAHO, SCIP, Premier, Leapfrog) | Patient Outcomes inclusive of patient satisfaction are tracked and trended by service line, nursing unit/department level and outpatient rehabilitation. Results are shared at unit/department level. Performance improvement process exists. | Condition specific patient outcomes inclusive of patient satisfaction (e.g., joint, spine, lower back pain (LBP), etc.) are tracked in addition to national and regulatory standards. Clear goals are established and success is part of performance review. Physicians and direct care providers involved in establishing, tracking and improving metrics. Results are leveraged internally and externally. |
| Margin | Cost accounting methodology exists within organization. Reports are available to review within senior leadership at an organizational level. | Margin management and improvement goals exist at an organization level. Initiatives to improve margin exist (i.e. all patients with a LOS > 3 days have internal review). | Service line margin goals are established, managed and communicated by service line. Service Line Manager responsible for managing both cost and revenue opportunities. Infrastructure is effective in executing change to enhance the service line and or product line's margin. |
| Volume | Inpatient and outpatient case volume goals exist at an organizational level. Case volume is routinely tracked. | Clearly defined goals are established and tracked by one of the service line, product line, or physician. Plan for volume growth exists and resource impact is understood. | Collaboration between the hospital and physicians exists to create long term service line strategy for volume growth. Implications on resources, facilities and care are understood and action plan developed. Physician and market specific goals established at a product line level to meet the service line growth strategy. |

TABLE 14

Engage Physicians Category

| Subcategories | Maturation Stages | | |
| --- | --- | --- | --- |
| | Infancy | Development | Maturity |
| Relationship/ Program Value to Physicians | Hospital-Medical staff relationship is professional and cordial. Service line discussions are productive. Physicians perceive value in alignment | Basic non-economic/foundational strategies being employed. Physicians are highlighted in service line or product line materials and programming. | Physicians actively involved in decisions that affect the care of their patients. Physicians perceive value in being associated with the program and perceive that their success is closely tied to program success. |
| Physician Leadership | Traditional medical staff leadership positions in place. Physicians actively work on product line specific initiatives that directly affect them (i.e. physician-specific order sets or protocols, OR improvements for their cases, etc.) | Key physicians in product line specific or overall service line leadership roles (may be paid or unpaid). Leadership roles are clearly defined and productive (i.e. clinical lead for product line team). Inconsistently engage other physicians in decision making. | Comprehensive, well-defined and active service line leadership structure in place (i.e. leadership council, defined product line leads). Leadership structure has accountability for care, margin and volume metrics (may or may not have bonus tied to metrics). Key physicians influence others for service line success. |
| Physician Engagement Plan | Hospital recognizes the need for an active engagement strategy and plan. Hospital has attempted isolated strategies with physicians. Strategies are not typically pro-active in nature, but rather reactive. | Hospital plan for service line physician engagement exists but not comprehensive in scope (physicians or strategy). Plan is being pro-actively developed but inconsistently or ineffectively communicated. | Hospital is deliberately and actively implementing a comprehensive short and long term strategic plan. Structure exists to ensure strategic plan is meeting the needs of the physicians, the hospital and the service line. |
| Percentage of Targeted Physicians Actively Engaged | 0-20% Engaged | 21-50% Engaged | 51-100% Engaged |

With respect to the Integrate Referral Sources category 10*e* of FIG. 2, service lines in each stage of maturation have been observed to exhibit the general characteristics set forth in Table 15 below.

TABLE 15

Integrate Referral Sources Category

| Subcategories | Maturation Stages | | |
| --- | --- | --- | --- |
| | Infancy | Development | Maturity |
| Resource | Consistent base of referral sources exist (i.e. employed PCP group, system "loyal" PCPs). Data collection of referrals obtained through admission data inconsistently and is not used in the strategic development of an integrated plan. | Referral base tracking and communication is broadened to include but is not limited to ED, Rheumatology, Occupational Medicine and Podiatry. Service line manager or hospital physician liaison assumes responsibility for integrating referral sources, establishing goals and communicating with leadership and surgeons. | Physician liaison assigned to the service line. Clearly defined goals are established and tracked relative to volume and demographic dispersion by product line. Referral sources have knowledge of service line services and specialties. Integration of non-physician/community referral sources exists and leveraged. |

TABLE 15-continued

Integrate Referral Sources Category

| | Maturation Stages | | |
|---|---|---|---|
| Subcategories | Infancy | Development | Maturity |
| Integration | General knowledge of needs, wants and expectations are understood for top referral sources. Tracking and improving referral relationships is minimal and occurs without integration of hospital and physician. | Educational needs of referral sources are identified. Education is provided independently by surgeons with existing referral sources on an as needed basis. Collaboration between referral source and surgeon for complex medical patients exists. | Hospital and surgeons have clear vision and plan for integrating referral sources. Education occurs routinely by specialty with CME credits provided with goal of ensuring right care at the right time by the right specialist. Objective data such as patient satisfaction and outcomes are leveraged with referral sources. |

With respect to the Link Care Continuum category 10f of FIG. 2, service lines in each stage of maturation have been observed to exhibit the general characteristics set forth in Table 16 below.

TABLE 16

Link Care Continuum Category

| | Maturation Stages | | |
|---|---|---|---|
| Subcategories | Infancy | Development | Maturity |
| Link Care Continuum | Care continuum is viewed in linear fashion. Elements of the care continuum exist but are episodic in nature (e.g., inpatient episode, outpatient episode, outpatient rehabilitation). | Care continuum linkages are identified at a product line level and extend beyond the hospital episode of care. Integration of each element of the care continuum is inconsistent. | Care continuum linkages are effectively, consistently and deliberately enhanced and integrated for each product line within the service line. Variations within the product line care continuum are clearly understood and leveraged to create distinction. |

With respect to the Build Brand Strategy category 10g of FIG. 2, service lines in each stage of maturation have been observed to exhibit the general characteristics set forth in Table 17 below.

TABLE 17

Build Brand Strategy Category

| | Maturation Stages | | |
|---|---|---|---|
| Subcategories | Infancy | Development | Maturity |
| Brand Establishment and Development | Brand and logo exists for service line. Web site has designation for the brand. | Content has been created unique to the service line and the specialty service provided. Some media advertising exists to create awareness in the community. | Hospital service line is well-established in the community. Brand is pervasive throughout the hospital advertising efforts and publications. Hospital signage for program exists. All elements of the continuum are tied to the brand. |

TABLE 17-continued

Build Brand Strategy Category

| | Maturation Stages | | |
|---|---|---|---|
| Subcategories | Infancy | Development | Maturity |
| Internal Awareness | Service line is represented in employee newsletters. | Communications within the hospital are a continuous effort. Signage reflecting brand are in areas where the service line staff are frequently present. Volunteers are included in service line communications. | Hospital has annual events for hospital employees which correspond to service line brand. Service line has own unique newsletter for staff. Brand is present throughout hospital campus. |
| Brand Relationship between Hospital and Physicians | Physicians are included in service line marketing activities. | Physicians have specifics to their practices and specialties in a referral guide and on the website. Participate in hospital based programs for the community. Liaison position exists and individual has been educated to help engagement effort. Quarterly bulletins are sent to physicians regarding program. | Physicians are included in the advertising by the hospital and play an active role in the development of programs geared toward the community and other physicians/referral sources. Physicians participate in the creation of branded educational materials. Physician and practice materials reflect brand. |
| Product Line Educational and Patient Materials | Product lines exist for subspecialty areas of the service line and are reflected in collaterals and website. | Product lines have unique materials under the umbrella brand for use in education and advertising. Product line outcomes are gathered & used for advertising to internal and external audiences. | Product lines have unique sub-brands with logos under the umbrella brand. Programs are developed specifically for the product lines and media advertising is done at the product line level. |
| Targeted Community Marketing | Hospital has periodic lectures to the community on campus for musculoskeletal service line. | Regular lectures occur at the hospital or elsewhere in the primary service area (PSA) which feature a cross section of the different subspecialties and clinical staff. Interactive programs/ clinics may also be occurring. Service line is involved in sponsored events. | A formal community calendar of musculoskeletal related events exists which features a combination of lectures and interactive programs. Programs occur both on campus and in strategic locations throughout the PSA and secondary service area (SSA). Strategic partners (e.g., sports team, outside organizations, vendors) are engaged in programming efforts. Participation is tracked to analyze patient conversion. |

Various maturation levels were analyzed and tested until the percentage scores most accurately coordinated with the general observational standards for the categories 10 and subcategories 12. As discussed above, percentage scores between approximately 0% and 44% were shown to coordinate with general observational standards for a program in the stage of infancy, percentage scores between approximately 45% and 79% were shown to coordinate with general observational standards for a program in the stage of development, and percentage scores between approximately 80% and 100% were shown to coordinate with general observational standards for a program in the stage of maturity.

Figure 3:
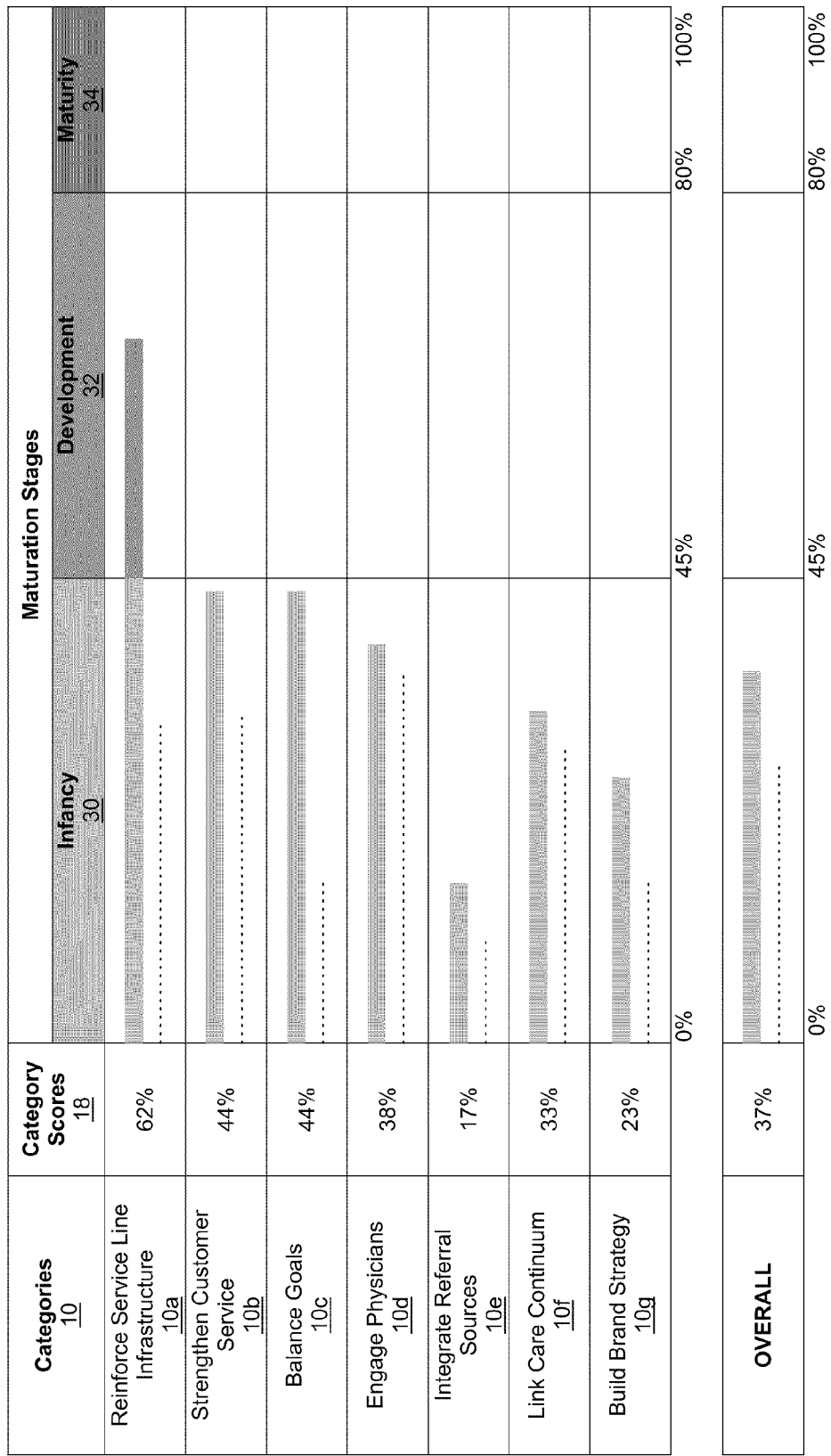
FIG. 3 is a chart illustrating a maturation scale of the present method.

Referring to the example of FIG. 3, an exemplary maturation scale 300 is illustrated graphically. The maturation scale 300 tracks the percentage scores 18 from all of the categories 10 and the overall percentage score 20 against the maturation stages or levels described above. The Reinforce Service Line Infrastructure category 10a is in a stage of development, while the remaining categories 10 are in a stage of infancy. The overall percentage score 20 of 37% indicates that the service line, as a whole, is in a stage of infancy.

Continuing to block 112 of FIG. 1, another step of the present method involves providing feedback to the hospital. According to an exemplary embodiment of the present invention, the feedback is in the form of a hard-copy report that is accessible by executives of the hospital, service line managers, product line managers, and coordinators, for example. According to another exemplary embodiment of the present invention, an electronic report is posted to a website and accessible via an internet network. The report may include both written and graphical summaries of the above-described method 100, such as maturation scale 300 shown in FIG. 3.

The feedback may include percentage scores 16 for each subcategory 12, percentage scores 18 for each category 10, and/or an overall percentage score 20. The feedback may also include raw scores 15. The percentage scores may be compared to previous percentage scores, such as the percentage scores for the previous year. For example, referring to the example of FIG. 3, percentage scores 18 and an overall percentage score 20 from the previous year are shown as dotted lines on maturation scale 300.

The feedback may also include a list of goals for the hospital and action steps for improving the maturation stage. In an exemplary embodiment, the goals are determined based on categories 10 and/or subcategories 12 that are rated lowest on maturation scale 300. In other words, the goals are determined based on scores in categories 10 and/or subcategories 12 that are lower than other scores of the same service line. For example, referring to the example of FIG. 3, the feedback may include action steps for the hospital to improve its integration of referral sources (category 10e). In another exemplary embodiment, the goals are determined based on categories 10 and/or subcategories 12 that are rated lower on maturation scale 300 than those of the hospital's competitors.

The feedback may also include a written summary of data gathered during the collecting step of block 102 (FIG. 1). For example, the feedback may include written summaries of demographic data, financial data, and patient care data.

According to an exemplary embodiment of the present invention, method 100 may be repeated on a routine basis. For example, method 100 may be repeated quarterly, bi-annually, or annually. In an exemplary embodiment, percentage scores 16 for each subcategory 12, percentage scores 18 for each category 10, and/or an overall percentage score 20 are compared to those of previous evaluation periods.

Figure 4:
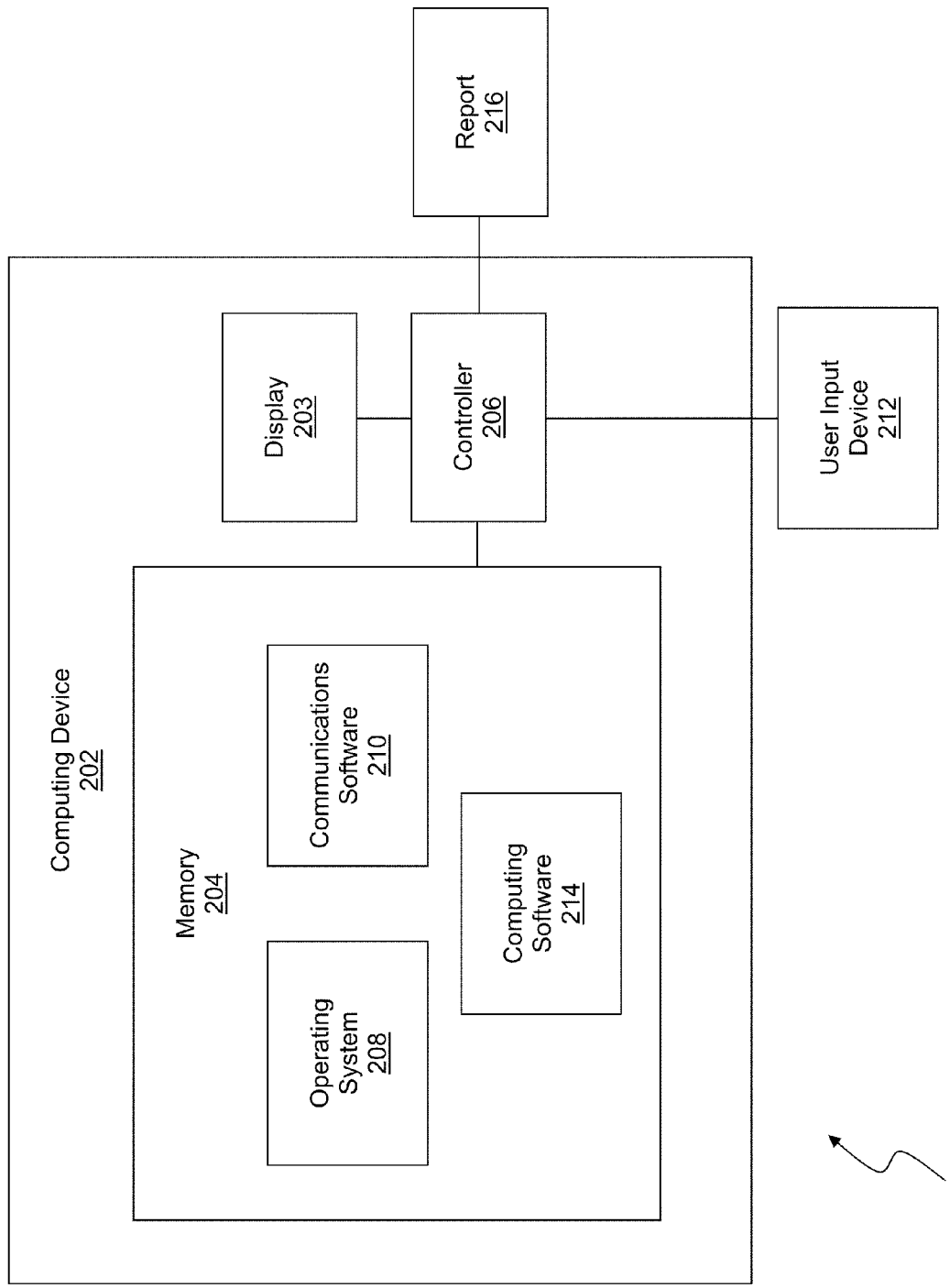
FIG. 4 is a schematic diagram illustrating an exemplary system of the present invention.

Referring to FIG. 4, an exemplary system 200 is provided for performing the above-described method. System 200 includes computing device 202, such as a general purpose computer or a portable computing device having display 203. Although system 200 is illustrated as including a single computing device 202, it should be understood that multiple computing devices 202 may be used together, such as over a network or other methods of transferring data.

Computing device 202 includes memory 204 and controller 206 that is able to access memory 204. Exemplary controllers include computer processors. Memory 204 is a computer readable medium and may be a single storage device or may include multiple storage devices, located either locally with system 200 or accessible across a network. Computer-readable media may be any available media that may be accessed by controller 206 of system 200 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by system 200.

As shown in FIG. 4, memory 204 of computing device 202 includes operating system 208 and communications software 210. Exemplary operating system software is WINDOWS™ operating system software available from Microsoft Corporation of Redmond, Wash. Communications software 210 allows computing device 202 to communicate with a local area network, a public switched network, a CAN network, any type of wired network, and any type of wireless network. An exemplary public switched network is the Internet. Exemplary communications software includes e-mail software, internet browser software, and other types of software which permit system 200 to communicate with other devices across a network.

Computing device 202 also includes user input device 212. User input device 212 may include buttons, knobs, keys, switches, a mouse, a touch screen, a roller ball, and other suitable devices for providing an input to system 200. As shown in FIG. 4, user input device 212 communicates with controller 206.

Memory 204 of computing device 202 further includes computing software 214. Exemplary computing software includes EXCEL™ available from Microsoft Corporation of Redmond, Wash. According to an exemplary embodiment of the present invention, computing software 214 is configured to calculate a percentage score 16 from a plurality of raw scores 15 as described above with respect to FIG. 2. Computing software 214 may also be configured to associate the calculated percentage score 16 with a stage or level of maturation and generate a maturation scale, such as the graphical maturation scale 300 of FIG. 3.

In operation, a user enters a plurality of raw scores 15 into computing device 202 via user input device 212. Then, computing software 214 calculates a percentage score 16 from the input raw scores 15, as described above. Finally, computing device 202 generates report 216. As discussed above, report 216 may be a hard-copy report that is sent to executives of the hospital, service line managers, product line managers, and coordinators, for example. Report 216 may also be an electronic report that is posted to a website and made available via an internet network. Report 216 may include both written and graphical summaries, such as maturation scale 300 of FIG. 3.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for managing and evaluating a service line of a hospital comprising the steps of:
    collecting data relevant to the service line of the hospital;
    awarding the service line of the hospital a raw score out of a possible score in each category of a plurality of categories based on the collected data, wherein awarding the raw score includes:
        awarding a raw score of zero to each category of the plurality of categories of the service line if one or more key elements of a care continuum for the category-are below a lower threshold established for the category; awarding a raw score of one to each category of the plurality of categories of the service line if one or more key elements of a care continuum for the category are between the lower threshold and an upper threshold established for the category; and awarding a raw score of two to each category of the plurality of categories of the service line if one or more key elements of a care continuum for the category are above the upper threshold established for the category;
    inputting the raw scores for each category of the plurality of categories into a computing device;
    calculating, with the computing device, a percentage score by dividing a sum of the raw scores for each category of the plurality of categories by a sum of the possible scores for the plurality of categories;

associating the percentage score with a stage of maturation; and reporting the stage of maturation to the hospital.

2. The method of claim 1, wherein the collecting data step comprises collecting at least one of demographic data, financial data, patient care experience data, patient care result data, infrastructure data, customer service data, strategic goal planning data, physician engagement data, referral source data, and brand strategy data.

3. The method of claim 1, wherein the stage of maturation comprises an infancy stage when the percentage score is between approximately 0% and 44%.

4. The method of claim 1, wherein the stage of maturation comprises a development stage when the percentage score is between approximately 45% and 79%.

5. The method of claim 1, wherein the stage of maturation comprises a maturity stage when the percentage score is greater than approximately 80%.

6. The method of claim 1, wherein the reporting step comprises providing the hospital with a graphical maturation scale that visually communicates the stage of maturation, wherein the graphical maturation scale is prepared by the computing device.

7. The method of claim 1, wherein the reporting step comprises posting an electronic report from the computing device to a website, the electronic report being accessible by the hospital via an internet network.

8. The method of claim 1, wherein the collecting step comprises collecting data relevant to a musculoskeletal service line of the hospital.

9. The method of claim 1, further comprising the step of providing feedback to the hospital to improve the stage of maturation for the plurality of categories, the plurality of categories having a lower percentage score than another plurality of categories.

10. The method of claim 1, further comprising the step of storing, in a non-transitory memory, a plurality of numeric standards associated with a plurality of stages of maturation, wherein the associating step comprises comparing, with the computing device, the percentage score with the plurality of numeric standards to identify the stage of maturation corresponding to the percentage score.

11. The method of claim 10, wherein the plurality of numeric standards comprise:
0% to 44%, which corresponds to an infancy stage;
45% to 79%, which corresponds to a development stage; and
80% or more, which corresponds to a mature stage.

12. The method of claim 1, wherein the service line of the hospital includes a first product line and a second product line, and wherein the awarding step is performed independently for the first product line and the second product line in at least one of the plurality of categories.

13. The method of claim 12, wherein the service line is a musculoskeletal service line, and wherein the first and second product lines are selected from the group consisting of: a joint replacement product line, a spine care product line, a hand and upper extremity product line, a foot and ankle product line, a rehabilitation product line, and a sports medicine product line.

14. The method of claim 12, wherein the awarding step is performed independently for the first product line and the second product line in a pre-surgical category, a day of surgery category, and a rehabilitation category.

15. The method of claim 1, further comprising the step of providing feedback to the hospital to improve the stage of maturation when the percentage score is lower than a corresponding percentage score for a competitor of the hospital.

16. A method for managing and evaluating a service line of a hospital comprising the steps of:
collecting data relevant to the service line of the hospital;
awarding the service line of the hospital a raw score out of a possible score in each category of a plurality of categories based on the collected data, wherein awarding the raw score includes:
awarding a raw score of zero to each category of the plurality of categories of the service line if one or more key elements of a care continuum for the category-are below a lower threshold established for the category; awarding a raw score of one to each category of the plurality of categories of the service line if one or more key elements of a care continuum for the category are between the lower threshold and an upper threshold established for the category; and awarding a raw score of two to each category of the plurality of categories of the service line if one or more key elements of a care continuum for the category are above the upper threshold established for the category;
inputting the raw scores for each category of the plurality of categories into a computing device;
calculating, with the computing device, a sum of the raw scores for each category of the plurality of categories;
classifying the service line of the hospital in one of an infancy stage, a development stage, and a maturity stage based on the sum of the raw scores for each category of the plurality of categories; and
providing feedback to the hospital based on the classifying step.

17. The method of claim 16, further comprising the step of calculating, with the computing device, a percentage score by dividing the sum of the raw scores for each category of the plurality of categories by a sum of the possible scores for each category of the plurality of categories, wherein the classifying step comprises classifying the service line of the hospital based on the percentage score.

18. The method of claim 17, wherein the classifying step comprises classifying the service line of the hospital in the infancy stage when the percentage score is between approximately 0% and 44%.

19. The method of claim 17, wherein the classifying step comprises classifying the service line of the hospital in the development stage when the percentage score is between approximately 45% and 79%.

20. The method of claim 17, wherein the classifying step comprises classifying the service line of the hospital in the maturity stage when the percentage score is greater than approximately 80%.

21. A method for managing and evaluating a service line of a hospital comprising the steps of:
collecting data relevant to the service line of the hospital;
evaluating the service line of the hospital in a plurality of categories, the plurality of categories selected from the group consisting of: patient care, infrastructure, customer service, strategic goal planning, physician engagement, referral sources, and brand strategy, wherein evaluating the service line includes awarding a raw score in each category of the plurality of categories based on the collected data, awarding the raw score including:

awarding a raw score of zero to each category of the plurality of categories of the service line if one or more key elements of a care continuum for the category-are below a lower threshold established for the category; awarding a raw score of one to each category of the plurality of categories of the service line if one or more key elements of a care continuum for the category are between the lower threshold and an upper threshold established for the category; and awarding a raw score of two to each category of the plurality of categories of the service line if one or more key elements of a care continuum for the category are above the upper threshold established for the category;

inputting information from the evaluating step into a computing device;

classifying the service line of the hospital, with the computing device, in one of an infancy stage, a development stage, and a maturity stage for each category of the plurality of categories; and providing feedback to the hospital based on the classifying step.

22. The method of claim 21, wherein the providing step comprises providing the hospital with a graphical maturation scale that visually communicates whether the service line of the hospital in classified in the infancy stage, the development stage, or the maturity stage for each category of the plurality of categories, wherein the graphical maturation scale is prepared by the computing device.

23. The method of claim 21, wherein the providing step comprises providing an electronic report accessible by the hospital via an internet network.

24. The method of claim 21, wherein the collecting step comprises collecting data relevant to a musculoskeletal service line of the hospital.

25. The method of claim 21, further comprising calculating, with the computing device, a combined score for each of the plurality of categories, at least one of the infrastructure category and the physician engagement category being weighted over another of the plurality of categories in the combined score.

* * * * *